(12) United States Patent
Samuelsson et al.

(10) Patent No.: US 11,260,111 B2
(45) Date of Patent: Mar. 1, 2022

(54) MUSSEL ADHESIVE PROTEIN PRODUCT AND APPLICATIONS THEREOF IN SUPPRESSION OF SKIN INFLAMMATIONS

(71) Applicant: JIANGYIN BENGT I. SAMUELSSON INSTITUTE OF LIFE SCIENCE CO., LTD., Jiangsu (CN)

(72) Inventors: Bengt Ingemar Samuelsson, Stockholm (SE); Min Gao, Jiangsu (CN)

(73) Assignee: Jiangyin Bengt I. Samuelsson Institute of Life Science Co., Ltd., Jiangyin (CN)

(*) Notice: Subject to any disclaimer, the term of this patent is extended or adjusted under 35 U.S.C. 154(b) by 0 days.

(21) Appl. No.: 16/732,436

(22) Filed: Jan. 2, 2020

(65) Prior Publication Data
US 2020/0215166 A1    Jul. 9, 2020

Related U.S. Application Data (63) Continuation of application No. 15/742,960, filed as application No. PCT/CN2015/084496 on Jul. 20, 2015, now Pat. No. 10,568,938.

(51) Int. Cl.

| | | |
|---|---|---|
| A61K 38/39 | (2006.01) | |
| A61K 9/06 | (2006.01) | |
| A61K 35/618 | (2015.01) | |
| A61K 9/12 | (2006.01) | |
| A61P 17/10 | (2006.01) | |
| A61P 31/22 | (2006.01) | |
| A61P 17/06 | (2006.01) | |
| A61P 17/00 | (2006.01) | |
| A61P 17/02 | (2006.01) | |
| A61P 29/00 | (2006.01) | |
| A61P 17/04 | (2006.01) | |
| A61K 9/00 | (2006.01) | |
| A61K 9/70 | (2006.01) | |
| A61K 38/17 | (2006.01) | |
| A61K 47/38 | (2006.01) | |
| A61K 47/10 | (2017.01) | |

(52) U.S. Cl.
CPC ............ *A61K 38/39* (2013.01); *A61K 9/0014* (2013.01); *A61K 9/06* (2013.01); *A61K 9/122* (2013.01); *A61K 9/7023* (2013.01); *A61K 35/618* (2013.01); *A61K 38/1767* (2013.01); *A61P 17/00* (2018.01); *A61P 17/02* (2018.01); *A61P 17/04* (2018.01); *A61P 17/06* (2018.01); *A61P 17/10* (2018.01); *A61P 29/00* (2018.01); *A61P 31/22* (2018.01); *A61K 47/10* (2013.01); *A61K 47/38* (2013.01)

(58) Field of Classification Search
None
See application file for complete search history.

(56) References Cited

U.S. PATENT DOCUMENTS

| | | |
|---|---|---|
| 6,395,269 B1 | 5/2002 | Fuller et al. |
| 10,485,848 B2 | 11/2019 | Gao et al. |
| 10,568,938 B2 | 2/2020 | Samuelsson et al. |
| 10,675,327 B2 | 6/2020 | Janson et al. |
| 11,090,360 B2 | 8/2021 | Janson et al. |
| 2002/0018787 A1 | 2/2002 | Kendall et al. |
| 2002/0168416 A1 | 11/2002 | Mitra et al. |
| 2002/0187201 A1 | 12/2002 | Bhonde et al. |
| 2003/0044470 A1 | 3/2003 | Wani et al. |
| 2005/0159396 A1 | 7/2005 | Harty |
| 2006/0275218 A1* | 12/2006 | Tamarkin ............... A61P 31/12 424/45 |
| 2006/0275370 A1 | 12/2006 | Chung et al. |
| 2013/0052712 A1 | 2/2013 | Cha et al. |
| 2018/0221444 A1 | 8/2018 | Janson et al. |
| 2018/0243371 A1 | 8/2018 | Gao et al. |
| 2020/0101135 A1 | 4/2020 | Gao et al. |

(Continued)

FOREIGN PATENT DOCUMENTS

| | | |
|---|---|---|
| CN | 1112831 A | 12/1995 |
| CN | 101348518 A | 1/2009 |
| CN | 101348520 A | 1/2009 |

(Continued)

OTHER PUBLICATIONS

International Search Report and Written Opinion for corresponding Application PCT/CN2015/084492 (dated Apr. 26, 2016).
Zhu et al., "The Research Progress on Mussel Adhesive Proteins," Advances in Marine Science 32(4):560-570 (2014).
Gao et al., "Review on Mussel Adhesive Protein," J. Anhui Agri. Sci. 39(32):19860-19862 (2011).
U.S. Appl. No. 15/742,969, filed Jan. 9, 2018, First Named Inventor: Jan Christer Janson.
U.S. Appl. No. 15/751,551, filed Feb. 9, 2018, First Named Inventor: Min Gao.

(Continued)

*Primary Examiner* — Christina Bradley
(74) *Attorney, Agent, or Firm* — Troutman Pepper Hamilton Sanders LLP (Rochester)

(57) ABSTRACT

Disclosed are applications of a mussel adhesive protein or preparations thereof in suppression of skin inflammations. Specifically disclosed are applications of a mussel adhesive protein, preparations thereof and applications thereof in dermatitis, eczema, skin ulcer, technologies related to burns (comprising skin grafting), perniones, surgical incisions, herpes, abrasions, scars, psoriasis, erythema multiforme, skin damage after radiotherapy, skin cancers, folliculitis, urticaria and drug eruption, and applications in sunburn, polymorphous light eruption, pathological alopecia (comprising hair transplant), acne vulgaris, rosacea (that is, acne rosacea), and the like, and applications in the treatment of otitis externa.

10 Claims, 2 Drawing Sheets

(56) References Cited

U.S. PATENT DOCUMENTS

2020/0323956 A1    10/2020    Janson et al.

FOREIGN PATENT DOCUMENTS

| | | |
|---|---|---|
| CN | 101585874 A2 | 11/2009 |
| CN | 101991840 A | 3/2011 |
| CN | 102302417 A | 1/2012 |
| CN | 103520766 A | 1/2014 |
| CN | 104323927 A | 2/2015 |
| CN | 104645313 A | 5/2015 |
| CN | 104645320 A | 5/2015 |
| CN | 104857552 A | 8/2015 |
| EP | 2471819 A2 | 7/2012 |
| GB | 2347349 A | 9/2000 |
| KR | 20110132498 A | 12/2011 |
| RU | 2043109 C1 | 9/1995 |
| WO | 92/21354 | 12/1992 |
| WO | 99/64580 | 12/1999 |
| WO | 00/71140 A2 | 11/2000 |
| WO | 01/05411 A1 | 1/2001 |
| WO | 2013/143077 A1 | 10/2013 |
| WO | 2014/186937 A1 | 11/2014 |

OTHER PUBLICATIONS

Wang et al., "Research Progress of Mussel Adhesive Proteins and its Derivatives Dopamine," Development and Application of Materials 29:101-104 (2014).

Yan et al., "Dopamine Controls Systemic Inflammation through Inhibition of NLRP3 Inflammasone," Cell 160:62-73 (2015).

Fei et al, "Application of MAP after Treatment of Atrophic Acne Scars with Micro-Plasma," J. Clin. Dermatol. 44(1):40-42 (2015).

Kaushik et al., "Biomedical and Clinical Importance of Mussel-Inspired Polymers and Materials," Mar. Drugs 13:6792-6817 (2015).

Li et al., "Progress of Research on Pharmaceutical Values of Mussels," Fisheries Science 23(11):43-44 (2004).

Liu et al., "Cytotoxicty Tests for the Mussel Adhesive Protein Dressing for Wound Healing," Chinese Journal of Tissue Engineering Research 17(38):6785-6790 (2013).

Wang et al., "The Mechanism of Adhesion and Film Forming and their Applied Research Progress of Mussel Adhesion Proteins," J. Functional Mat. 14:14013-14020 (2014).

Couch et al., "Anti-Inflammatory Activity in Fractionated Extracts of the Green-Lipped Mussel," The New Zealand Medical Journal 95(720):803-806 (1982).

Park et al., "Antioxidant and Anti-Inflammatory Activities of Protein Hydrolysates from Mytilus Edulis and Ultrafiltration Membrane Fractions," J. Food Biochem. 38:460-468 (2014).

Kim et al., "Mussel-Mimetic Protein-Based Adhesive Hydrogel," Biomacromolecules 15:1579-1585 (2014).

Kim et al., "Purification of a Novel Anticancer Peptide from Enzymatic Hydrolysate of Mytilus coruscus," J. Microbiol. Biotechnol. 22(10):1381-1387 (2012).

Nichols et al., "Skin Photoprotection by Natural Polyphenols: Anti-Inflammatory, Antioxidant and DNA Repair Mechanisms," Arch. Dermatol. Res. 302:71-83 (2010).

International Search Report and Written Opinion for International Patent Application Serial No. PCT/CN2015/084494 (dated Apr. 26, 2016).

International Search Report and Written Opinion for International Patent Application Serial No. PCT/CN2016/095364 (dated Oct. 8, 2016) (English translation of International Search Report only).

International Search Report and Written Opinion for International Patent Application Serial No. PCT/CN2015/087011 (dated May 20, 2016) (English translation of International Search Report only).

Rainsford et al., "Gastroprotective and Anti-Inflammatory Properties of Green Lipped Mussel (*Perna canaliculus*) Preparation," Arzneimittelforschung 30(12):2128-32 (1980) (Abstract).

Burzio, "Cross-Linking in Adhesive Quinoproteins: Studies with Model Decapeptides," Biochem. 39:11147-11153 (2009).

Wang et al., "Purification and Characterisation of a Novel Antioxidant Peptide Derived from Blue Mussel (*Mytilus edulis*) Protein Hydrolysate," Food Chem. 138:1713-1719 (2013).

Bandara et al., "Marine Mussel Adhesion; Biochemistry, Mechanisms, and Biomimetics," J. Adhes. Sci. and Tech. 27(18-19):2139-2162 (2012).

Gupta et al., "The Treatment of Melasma: A Review of Clinical Trials," J. Am. Acad. Dermatol. 55(6):1048-1065 (2006).

Slominski et al., "Melanin Pigmentation in Mammalian Skin and Its Hormonal Regulation," Physiol. Rev. 84(4):1155-1228 (2004).

Sklar et al., "Effects of Ultraviolet Radiation, Visible Light, and Infrared Radiation on Erythema and Pigmentation: A Review," Photochem. Photobiol. Sci. 12(1):54-64 (2013).

Lee et al., "Mussel-Inspired Adhesives and Coatings," Annu. Rev. Mater. Res. 41:99-132 (2011) [Author Manuscript].

Wang et al., "Adhesion Mechanism of Mussels," Chemistry of Life 27(6):490-494 (2007).

\* cited by examiner

*Fig. 1*

| VAS | 0d | 3d | 7d | 14d |
|---|---|---|---|---|
| Test group | 5.3 | 4.2 | 2.4 | 0.7 |
| Control group | 6.1 | 4.6 | 3.3 | 3.1 |

MUSSEL ADHESIVE PROTEIN PRODUCT AND APPLICATIONS THEREOF IN SUPPRESSION OF SKIN INFLAMMATIONS

This application is a continuation of U.S. patent application Ser. No. 15/742,960, filed Jan. 9, 2018, which is a national stage application under 35 U.S.C. § 371 of PCT Application No. PCT/CN2015/084492, filed Jul. 20, 2015.

FIELD OF THE INVENTION

The present invention substantially relates to the technical field of drugs, cosmetics, medical products, disinfecting products, healthcare products, food, and household chemicals, and more specifically, relates to a mussel adhesive protein product and a use thereof for inhibiting skin inflammation.

DESCRIPTION OF THE RELATED ART

As the first physiological barrier and the largest organ of human body, skin always participates in functional activities of the body, maintains the unity of opposites between the body and natural environment. Moreover, any abnormal conditions of the body could be reflected from the skin surface as well. Skin consists of epidermis, dermis and subcutaneous tissues, and comprises numerous auxiliary organs, such as follicle glands, sebaceous glands, finger nails, toe nails, blood vessels, lymphatic ducts, nerves and muscles. Skin has almost perfect capabilities of physiological protection, such as barrier function, perception function, body temperature regulation function, absorption function, secretion and excretion function, etc., and plays a very important role in maintaining the body health.

Inflammation is a defensive response by an organism to irritation, with manifestations such as redness, swelling, heat, pain, and dysfunction. In an inflammatory process, on one hand, a damage factor directly or indirectly damages tissues and cells, and on the other hand, the damage factor is diluted, killed and surrounded through inflammatory hyperemia and exudation. At the same time, the damaged tissues are repaired and healed through regeneration of parenchymal and interstitial cells. Therefore, it can be stated that inflammation is a unified process of damage and anti-damage.

Mussel adhesive protein (MAP), also known as *Mytilus edulis* foot protein (Mefp), is a special protein secreted by marine shellfish, such as *Mytilus edulis* Linnaeus, *Mytilus coruscus* and *Perna viridis*. Mussels are typically attached, in groups, to coastal reefs or ship bottom and have the ability to resist wave impacts in coastal waters. In fact, mussels can be extremely firmly attached to a base of almost any material, such as metals, wood, glass, etc. The main reason why mussels have the above characteristic is that such a special adhesive protein can be produced and stored inside the byssus gland thereof. Mussels release the adhesive protein through byssus to a surface of a solid like rock, to form a water-proof bonding and consequently fix itself.

At present, 11 adhesive protein subtypes have been identified in mussels, including mefp-1, mefp-2, mefp-3, mefp-4, mefp-5, mefp-6, the collagens pre-COL-P, pre-COL-D, pre-COL-NG and the mussel feet matrix proteins PTMP and DTMP (Yaoyao Zhu, et al., Advances in Marine Science, 2014, 32(4): 560-568). MAP has 2 structural characteristics: (1) comprising lysine, such that the protein carries a high loading of positive charge; (2) comprising 3,4-dihydroxy-phenylalanine (DOPA, Levodopa). Human cells and tissues carry negative charges. MAP is tightly bonded to the cells and tissues through the static interaction between its own positive charge and the negative charge of the human cells and tissues, thereby playing a role of protection and treatment. In addition, DOPA is oxidized to produce o-diquinone, which may be crosslinked with unoxidized DOPA to form a membrane or a reticular support, such that the proteins are attached to human body surface in a tighter and firmer manner to play a protective role. MAP is a macromolecular protein, and it needs about 3-10 days to be completely degraded in human body. It has superior ability to be attached to cells and tissues, such that MAP is stable in a local part to continuously play its role.

Despite the above characteristics of MAP, MAP products are applied in a very limited number of fields at present. The MAP production is mainly controlled by BD Biosciences from the U.S., Kollodis from South Korea, and Biopolymer from Sweden. However, these companies' products are either directly used as an MAP solution or stored as a freeze-dried powder and dissolved prior to use. Their applications are mainly limited to micro-cellular bonding and tissue adhesive agents. There are also reports that MAP is used for fetal membrane repair, seawater corrosion-resistant coating, cardiac drug carrier, etc.

SUMMARY OF THE INVENTION

One object of the present invention is to provide MAP products.

MAP used herein refers to one or a mixture of several selected from the group consisting of 11 MAP subtypes, including mefp-1, mefp-2, mefp-3, mefp-4, mefp-5, mefp-6, the collagens pre-COL-P, pre-COL-D, pre-COL-NG and the mussel feet matrix proteins PTMP and DTMP, that are currently known and purified from marine mussels, such as *Mytilus edulis* Linnaeus, *Mytilus coruscus*, and *Perna viridis*, in bivalve mollusks of Mytilidae. MAP used herein may have a pH value, in an aqueous solution, in a range of pH 1.0-7.0, and in particular, in a range of pH 3.0-6.5 for better therapeutic results thereof.

MAP used herein may be obtained using the following preparation methods, for example, a method for separating and purifying MAP by using mixed adsorption chromatography according to the Chinese Patent No. ZL200710179491.0, a method for purifying MAP by using carboxymethyl ion exchange chromatography according to the Chinese Patent No. ZL200710179492.5, and a method for separating and purifying MAP by using salting out and dialysis according to the Chinese Patent No. ZL200910087567.6.

MAP used herein may be in a form of solution or freeze-dried powder, and in particular, the MAP concentration in a product may be 0.1-15.0 mg/ml. When the concentration is overly low, MAP does not have a good effect, and when the concentration is overly high, it may cause cytotoxicity, skin irritation, etc., which is not favorable for treatment of skin inflammations.

MAP used herein may also be combined with excipients to prepare a liquid formulation. An exemplary MAP liquid formulation is prepared by dissolving or diluting an MAP stock solution or freeze-dried powder to a certain concentration or pH value, and the solution used for dissolution or dilution could be water, physiological saline, phosphate solution, acetate solution, borate solution, etc. MAP in the final product may have a pH value in a range of pH 1.0-7.0, and in particular, in a range of pH 3.0-6.5 for better therapeutic results thereof.

MAP used herein may also be combined with excipients to prepare a gel formulation. An exemplary MAP gel formulation is prepared by mixing an MAP solution or freeze-dried powder with a gel matrix material, and the gel matrix material may be one or any combination of cellulose derivatives, Carbomer and Alginates, gummi tragacanthae, gelatin, pectin, Carrageenan, gellan gum, starch, Xanthan gum, cationic guar gum, agar, noncellulosic polysaccharides, vinyl polymers, acrylic resins, polyvinyl alcohol and carboxyvinyl polymer.

MAP used herein may also be combined with excipients to prepare a lotion. An exemplary MAP lotion is made by mixing an MAP solution or freeze-dried powder with a lotion matrix, and said lotion matrix may comprise one or any combination of cellulose derivatives, glycerin, noncellulosic polysaccharides, and propanediol.

MAP used herein may also be combined with excipients to prepare a paste. An exemplary MAP paste is made by mixing MAP with a paste matrix material, and said paste matrix material may comprise glycerin, vaseline, paraffin, etc.

Those skilled in the art may choose the above formulations or other appropriate formulations according to characteristics of clinical indications and skin damage at different stages.

MAP used herein may further be combined with a matrix material to prepare a dressing or a therapy patch for application on a skin surface. The liquid of an exemplary MAP therapy patch may be an MAP solution or a combination thereof with one or more of cellulose derivatives, Carbomer and Alginates, gummi tragacanthae, gelatin, pectin, Carrageenan, gellan gum, starch, Xanthan gum, cationic guar gum, agar, noncellulosic polysaccharides, vinyl polymers, acrylic resins, polyvinyl alcohol or carboxyvinyl polymer, gelatin, isinglass, pectin, alginates, glycerin, vaseline, paraffin, polyethylene glycol, vitamins, and glutathione. The above MAP solution or composition impregnates a matrix material, such as gauze, non-woven cloth, or silk paper, and the therapy patch may be, for example, band-aid, facial mask, eye mask, hand mask, foot mask, etc.

MAP used herein may also be prepared into a foam formulation. An exemplary MAP foam formulation is made by mixing an MAP solution or freeze-dried powder with a foaming agent matrix, and said foaming agent matrix material may comprise one or any combination of hydroxypropyl methyl cellulose, gelatin, polyethylene glycol, sodium dodecyl sulfate, sodium fatty alcohol polyoxyethylene ether sulfonate, corn gluten powder and acrylamide. A particular advantage is that the foaming agent releases pressure during the defoaming process, which is more favorable for attachment, permeation and onset of MAP at an affected part. At the same time, the foaming agent has a long defoaming time, which extends the action time and makes the MAP onset more significant.

Components known in the art to be capable of strengthening moisturizing and anti-oxidation capabilities, such as glycerin, polyethylene glycol, vitamins, and glutathione, may be further added into the above various products that contain MAP to further improve the moisturizing and anti-oxidation capabilities.

All the above formulations may be prepared with methods known in the art, and reference may be made to, for example, "Pharmaceutical Preparation", for detailed operating steps.

MAP used herein may be used as a main raw material to prepare a drug along with a pharmaceutically acceptable carrier. The drug may be a liquid formulation, a gel formulation, a lotion, a paste, a therapy patch, or a foam formulation. The drug may be applied externally, and in particular, may be applied on the skin externally.

MAP used herein may be used as a main raw material to prepare a medical device. The term used herein, medical device, refers to a material, or other similar or related objects, used, directly or indirectly, on human body. The medical device may be a liquid formulation, a gel formulation, a lotion, a paste, a therapy patch, or a foam formulation. The medical device may be applied externally, and in particular, may be applied on the skin externally.

MAP used herein may be used as a main raw material to prepare cosmetics along with excipients that are acceptable in the field of cosmetics. The cosmetics may be a liquid formulation, a gel formulation, a lotion, a paste, a therapy patch, or a foam formulation. The cosmetics may be applied externally, and in particular, may be applied on the skin externally.

MAP used herein may be used as a main raw material to prepare a disinfecting product along with excipients that are acceptable in the field of disinfecting products. The term used herein, disinfecting product, refers to a disinfectant, a disinfecting device, a sanitary product and a disposable medical article that kills or eliminates pathogenic microorganisms in the environment in a chemical, physical or biological manner. The disinfecting product may be a liquid formulation, a gel formulation, a lotion, a paste, a therapy patch, or a foam formulation. The disinfecting product may be applied externally, and in particular, may be applied on the skin externally.

MAP used herein may be used as a main raw material to prepare a healthcare product or food along with excipients that are acceptable in the field of healthcare products or foods. The healthcare product or food may be a liquid formulation, a gel formulation, a lotion, a paste, a therapy patch, or a foam formulation. The healthcare product or food may be applied externally or edible, and in particular, may be applied on the skin externally.

MAP used herein may be used as a main raw material to prepare a household chemical along with excipients that are acceptable in the field of household chemicals. The term used herein, household chemicals, refers to a chemical product for daily use, including shampoo, bath gel, etc. The household chemical may be a liquid formulation, a gel formulation, a lotion, a paste, a therapy patch, or a foam formulation. The household chemical may be applied externally, and in particular, may be applied on the skin externally.

Another object of the present invention is to provide a use of MAP products in inhibiting skin inflammation.

The term used herein, inhibit, refers to a process that mitigates the original damages after a tissue or organism is irritated. The term used herein, treat, refers to a process that intervenes or changes a specific health state and activities taken to relief suffering.

Skin inflammation is a skin disease and one of the common diseases and frequently-occurring diseases that severely affect human health. When the skin's barrier function is weakened, inflammations inside the skin, such as coarseness, redness, itching, eczema, and dryness, will occur, and the causes are external and internal. Internal causes involve body conditions, hormone level, pressure, etc.; external causes include, for example, UV, allergens, heat and other irritations. Only through treatments that inhibit the inflammation, can the skin condition be improved.

Small lumps, refractory ulcers, and pigmented spots caused by skin inflammation, if not treated promptly, will develop to basal cell carcinoma, squamous cell carcinoma, and malignant melanoma. Basal cell carcinoma and squamous cell carcinoma are just some small spots with coarse surface in the beginning, which are slightly redder or whiter than surrounding skin, or may be tiny lumps or small ulcers that tend to bleed, are slow to heal, or do not heal. Early symptoms of malignant melanoma usually include the appearance of skin pigmented spots, change of mole colors, appearance of new moles, and the production of brown and black pigment cells due to pathological accumulation.

Dermatitis is a general term for skin inflammatory diseases caused by various internal and external infectious or non-infectious factors, and its causes of disease and clinical manifestations are complex and diversified. Clinically, a certain dermatitis is often defined to be a certain dermatitis according to the cause of disease, disease location or other clinical features. For example, dermatitis caused by contact with a substance is referred to as contact dermatitis, dermatitis caused by internal use of a drug is referred to as dermatitis medicamentosa, etc.

Eczema is a skin inflammatory reaction with strong itching caused by a variety of internal and external factors. It has three phases, acute, sub-acute, and chronic. In the acute phase, there is a tendency of exudation, while the chronic phase includes infiltration and hypertrophy. Some patients directly have chronic eczema. Skin lesions have characteristics such as multi-form, symmetric, itchy and easily recurring.

Skin ulcer is a common disease and frequently-occurring disease in surgery of traditional Chinese medicine, which is a topical disease with ulcers on the skin as the main clinical manifestation, inability to heal for a long period as clinical feature, and with skin tissues missing, damaged, liquefied, infected, and necrotic. As the ulcerated surface is hard to heal and costly, it causes great mental pressure and economic loss to the patients, and severely affects the body health and life quality of the patients.

Herpes refers, in a broad sense, to diseases caused by viruses in herpetoviridae. At present, it is known that eight viruses in this family could infect humans, and these viruses are collectively referred to as human herpes viruses. Among them, the common ones include varicella zoster virus, herpes simplex virus, etc., and herpes could infect a number of human organs.

Acne is a follicular (pilosebaceous unit) chronic, inflammatory skin disease, the occurrence of which is closely related to main factors like hypersteatosis, blocked pilosebaceous ducts, bacterial infection and inflammatory reaction. It tends to occur in youth, and would often naturally mitigate or heal after puberty. Clinical manifestations are characterized by multiform skin lesions on the face, such as pimple, rash, pustule, nodus, etc.

Hives is a localized edema reaction due to expansion of skin and mucosal small vessels and increased permeability, which typically subsides within 2 to 24 hours, but will recur to produce new skin rashes. The causes of hives are very complicated, and causes cannot be identified for about ¾ of the patients, in particular in the case of chronic hives. Common causes mainly include: Food and food additives; inhaled substances; infection; drugs; physical factors, such as mechanical irritation, coldness and heat, sunshine, etc.; insect bites; mental factors and endocrine changes; genetic factors, etc.

Polymorphous sunlight eruption or polymorphous light eruption is a photoallergic reaction, which is a recurrent, chronic, multiform, and photosensitive skin disease. Currently, it is believed that this might be a delayed photoallergy caused by a variety of reasons. A variety of photo-allergens are involved with this.

Early manifestations of skin cancers are mostly erythema-like skin lesions, accompanied by scaly desquamation or crust formation. It is difficult to differentiate its histological type through observation with naked eye only, and moreover, it tends to be mistaken as benign skin diseases like psoriasis, eczema. The diagnosis can be confirmed often through pathologic examination. Skin cancers have a low incidence rate in China, but are one of the common malignant tumors among white people. Basal cell carcinoma is the most common skin cancer.

Psoriasis, commonly known as serpedo, is a chronic, inflammatory skin disease with a relatively long course of disease and tendency to recur. Some patients almost never heal in their entire life. Clinical manifestations of psoriasis mainly include erythema and scales. It could occur over the whole body, more commonly seen on scalp and limb extension sides.

Burns usually refer to tissue damages caused by heat, including hot liquids (water, soup, oil, etc.), steam, high-temperature gases, flame, red-hot metal liquid or solid (e.g. melted steel, steel ingot), and the tissues mainly refer to skin and/or mucosa, and in serious cases, subcutaneous and/or submucous tissues, such as muscles, bones, joints, and even internal organs, could be damaged.

Frostbite means recurrent erythema and swelling damage on local skin caused by cold weather, and in serious cases, blisters and ulcers could appear. The course of the disease is slow, and it heals on its own when the weather becomes warm, but tends to recur.

Operative incision refers to skin damage caused by surgeries.

Bruise is an injury caused by friction due to a blunt mechanical force, with epidermis peeled off and rolled as the main manifestation. It may present with scratches, scores, percussion marks, pressing marks, pressing and scratching marks, etc.

Scar is a general term of histopathological changes to the morphology of normal skin tissues caused by various traumas, which is a necessary product from the process of repairing human body traumas. When the scar growth exceeds a certain limit, various complications will take place, e.g. destruction to the appearance, dysfunctions, movement disorders, etc., in particular in the case of scars from burning, scalding, and severe injuries.

Erythema multiforme is an acute inflammatory skin disease, which is self-limited. The rash is multiform, including erythema, papule, hive, blister, etc. The characteristic skin lesion is a target lesion, i.e. iris lesion. There are various degrees of mucosal damages, and damages to internal organs in some cases.

Post radiation therapy skin damage means skin ulceration due to radiation therapy.

Folliculitis is a suppurative inflammation due to bacterial infection of the entire hair follicle. At the beginning, red papules appear, which gradually evolve into papular pustules. They are isolated and can feel slight pain. For adults, it mostly occurs in hairy positions, and for children, it tends to occur on the head. The rashes sometimes join each other, and small bald patches could form after healing.

Pathological alopecia is hair loss caused by pathological factors, such as some mental pressures, acute or chronic contagious diseases, various skin diseases, endocrine disorder, physical or chemical factors, neural factors, nutrition factors, etc.

Seborrheic dermatitis is also referred to as seborrheic eczema, which is a chronic, papulosquamous and inflammatory skin disease that occurs at positions with a lot of sebaceous glands. The skin lesion mostly begins at the scalp, and gradually spread downwards to eyebrow, nasolabial fold, cheek, behind the ears, upper chest, intrascapular area, periumbilical area, genital area, groin, etc.

External otitis is a chronic, localized and suppurative disease of external auditory meatus skin, also referred to as localized external otitis. It occurs at the cartilage part of external auditory meatus, and is one of the common otologic diseases. External otitis is mostly caused by damages to the external auditory meatus skin as a result of ear picking or by water accumulation in the external auditory meatus during swimming or showering, such that local epidermis is softened and prone to bacterial infection.

Surprisingly, the inventors find that MAP has excellent effects on mitigating erythema, redness and swelling, edema, blisters, and bullous pemphigoid caused by various skin inflammations, inhibiting exudation of subcutaneous tissue fluid, mitigating coarse pores, and suppressing itching and pain caused by inflammations.

Surprisingly, the inventors find that MAP can be used to treat dermatitis, eczema, sunburn, polymorphous sunlight eruption, skin ulcer, burn surgery (including skin grafting), frostbite, operative incision, herpes, bruise, scar, psoriasis, erythema multiforme, post radiation therapy skin damage, skin cancer, seborrheic dermatitis, pathological alopecia (including skin grafting), regular acne, acne rosacea (i.e. brandy nose), folliculitis, hives, drug eruption, polymorphous sunlight eruption, and external otitis.

DETAILED DESCRIPTION OF THE PREFERRED EMBODIMENTS

Embodiments of the present invention comprise:
1. Use of MAP in treatment of skin inflammation.
2. The use of MAP according to Embodiment 1, wherein the MAP is one or a mixture of several selected from the group consisting of subtypes mefp-1, mefp-2, mefp-3, mefp-4, mefp-5, mefp-6, the collagens pre-COL-P, pre-COL-D, pre-COL-NG, the mussel feet matrix proteins PTMP and DTMP.
3. The use of MAP according to Embodiment 1, wherein the MAP concentration may be 0.1-15.0 mg/ml.
4. The use of MAP according to Embodiment 1, wherein the MAP may be a liquid formulation, a gel formulation, a lotion, a paste, a therapy patch, or a foam formulation in use.
5. The use of MAP according to Embodiment 1, wherein MAP in the final product is in a range of pH 1.0-7.0, and in particular, in a range of pH 3.0-6.5.
6. The use of MAP according to any one of Embodiments 1-5, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.
7. The use of MAP according to any one of Embodiments 1-5, wherein the skin inflammation is selected from: sunburn, polymorphous sunlight eruption, pathological alopecia (including hair transplant), regular acne, and acne rosacea (i.e. brandy nose).
8. The use of MAP according to any one of Embodiments 1-5, wherein the skin inflammation is external otitis.
9. Use of MAP as an active ingredient in a composition for treatment of skin inflammation, wherein the composition is a liquid formulation, a gel formulation, a lotion, a paste, a therapy patch, or a foam formulation in use.
10. The use of MAP according to Embodiment 9, wherein the composition is a composition for external application on the skin.
11. A drug for treatment of skin inflammation, comprising MAP and a pharmaceutically acceptable carrier, wherein the MAP concentration is 0.1-15.0 mg/ml.
12. A medical device for treatment of skin inflammation, comprising MAP and a carrier acceptable in the field of medical devices, wherein the MAP concentration is 0.1-15.0 mg/ml.
13. A cosmetic for treatment of skin inflammation, comprising MAP and a carrier acceptable in the field of cosmetics, wherein the MAP concentration is 0.1-15.0 mg/ml.
14. A disinfecting product for treatment of skin inflammation, comprising MAP and a carrier acceptable in the field of disinfecting products, wherein the MAP concentration is 0.1-15.0 mg/ml.
15. A healthcare product or food for treatment of skin inflammation, comprising MAP and a carrier acceptable in the field of healthcare products or foods, wherein the MAP concentration is 0.1-15.0 mg/ml.
16. A household chemical for treatment of skin inflammation, comprising MAP and a carrier acceptable in the field of household chemicals, wherein the MAP concentration is 0.1-15.0 mg/ml.
17. Use of MAP in a drug for treatment of skin inflammation, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.
18. Use of MAP in a drug for treatment of skin inflammation, wherein the skin inflammation is selected from: sunburn, polymorphous sunlight eruption, pathological alopecia (including hair transplant), regular acne, and acne rosacea (i.e. brandy nose).
19. Use of MAP in a drug for treatment of skin inflammation, wherein the skin inflammation is external otitis.
20. Use of MAP in a medical device for treatment of skin inflammation, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.

21. Use of MAP in a medical device for treatment of skin inflammation, wherein the skin inflammation is selected from: sunburn, polymorphous sunlight eruption, pathological alopecia (including hair transplant), regular acne, and acne rosacea (i.e. brandy nose).

22. Use of MAP in a medical device for treatment of skin inflammation, wherein the skin inflammation is external otitis.

23. Use of MAP in a cosmetic for treatment of skin inflammation, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.

24. Use of MAP in a cosmetic for treatment of skin inflammation, wherein the skin inflammation is selected from: sunburn, polymorphous sunlight eruption, pathological alopecia (including hair transplant), regular acne, and acne rosacea (i.e. brandy nose).

25. Use of MAP in a cosmetic for treatment of skin inflammation, wherein the skin inflammation is selected from: external otitis.

26. Use of MAP in a disinfecting product for treatment of skin inflammation, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.

27. Use of MAP in a disinfecting product for treatment of skin inflammation, wherein the skin inflammation is selected from: sunburn, polymorphous sunlight eruption, pathological alopecia (including hair transplant), regular acne, and acne rosacea (i.e. brandy nose).

28. Use of MAP in a disinfecting product for treatment of skin inflammation, wherein the skin inflammation is external otitis.

29. Use of MAP in a healthcare product or food for treatment of skin inflammation, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.

30. Use of MAP in a healthcare product or food for treatment of skin inflammation, wherein the skin inflammation is selected from: sunburn, polymorphous sunlight eruption, pathological alopecia (including hair transplant), regular acne, and acne rosacea (i.e. brandy nose).

31. Use of MAP in a healthcare product or food for treatment of skin inflammation, wherein the skin inflammation is selected from: external otitis.

32. Use of MAP in a household chemical for treatment of skin inflammation, wherein the skin inflammation is selected from: dermatitis, eczema, skin ulcer, burn surgery (including skin grafting), frostbite, operative incision, herpes, bruise, scar, psoriasis, erythema multiforme, chemo rash, skin cancer, folliculitis, hives, and drug eruption.

33. Use of MAP in a household chemical for treatment of skin inflammation, wherein the skin inflammation is selected from: sunburn, polymorphous sunlight eruption, pathological alopecia (including hair transplant), regular acne, and acne rosacea (i.e. brandy nose).

34. Use of MAP in a household chemical for treatment of skin inflammation, wherein the skin inflammation is external otitis.

35. A foam formulation for treatment of skin inflammation, comprising MAP as the main active ingredient and a foaming agent matrix material, said foaming agent matrix material being one or any combination of hydroxypropyl methyl cellulose, gelatin, polyethylene glycol, sodium dodecyl sulfate, sodium fatty alcohol polyoxyethylene ether sulfonate, corn gluten powder and acrylamide, wherein the MAP concentration is 0.1-15.0 mg/ml.

The present invention will be further described below with reference to specific embodiments. It should be noted that, when a drug, medical device, cosmetic, disinfecting product, healthcare product or food, or household chemical formed from MAP or various formulations of MAP according to the present invention is applied on a subject, it can be used on the indications described above and exhibits the functions described above. All formulations within the scope of the present invention have been tested, and only a small portion thereof is described below in the embodiments for the purpose of description; however, they shall not be construed as limitations to the present invention.

Unless otherwise specifically described, all reagents used in the present invention are commercially available on the market.

Example 1: Use of MAP Liquid Medical Device in Treatment of Eczema

Take 1 ml of an MAP solution with concentration at 20.0 mg/ml, add 9 ml of 0.1% citric acid solution, and prepare an MAP aqueous solution medical device with concentration at 2.0 mg/ml.

Gather 20 patients with acute eczema as diagnosed by dermatologists for test. Eczema locations are not limited for the selected patients, the affected areas are 1-2% TBSA (total body surface area), and the affected areas have patches of erythema, dense or dispersed small papules and blisters, or large patches of weeping liquid and ulceration.

For the selected patients, spray the above MAP aqueous solution medical device on the affected part, 3 times per day, and spray 3-5 times each time until the affected part is completely covered by the MAP aqueous solution medical device. After sprayed with the MAP aqueous solution medical device, itching at the affected part is significantly reduced within 2 to 10 min, the visual analogue score VAS goes from 6.0-8.0 prior to the drug administration down to 1.0-3.0, and the duration of itching relief can last 2 to 10 h (see Table 1). As the time of drug use is extended, the itching relief duration is extended, and the use interval is extended, which does not show any drug dependence.

After 3 days of continuous spraying of MAP, 4 patients have their eczema areas fully healed, as indicated by disappearance of erythema, papules and blisters, and no exudation at the affected part. After 5 days of continuous spraying, all patients are cured.

TABLE 1

| | |
|---|---|
| Average onset time (min) | 3.3 ± 1.2 |
| Average VAS prior to use | 7.6 ± 0.9 |
| Average VAS after use | 1.4 ± 0.3 |
| Average itching relief duration (h) | 8.2 ± 2.1 |
| Average healing time (d) | 3.9 ± 1.0 |

Example 2: Use of MAP Gel Medical Device in Treatment of Eczema

Add 10 g sodium carboxymethyl cellulose into 20 ml deionized water, place in a bath at 90° C. for 30 min until complete dissolution to obtain a gel matrix. Add 2.5 ml of an MAP solution with concentration at 10.0 mg/ml into the gel matrix, add slowly under constant stirring, and mix homogeneously to form an MAP gel medical device, wherein the MAP concentration is 1.1 mg/ml.

Gather 20 patients with acute eczema. Eczema locations are not specified for the selected patients, the affected areas are 1-2% TBSA (total body surface area). The patients are diagnosed by dermatologists, sign the informed consent form, and then join the clinical test. The affected areas of the patients have patches of erythema, dense or dispersed small papules and blisters, or large patches of weeping liquid and ulceration.

For the selected patients, apply the above MAP gel medical device on the affected part, 3 times per day, and spray 3-5 times each time until the affected part is completely covered by the MAP gel medical device. After applied with the MAP gel medical device, itching at the affected part is significantly reduced within 1 to 7 min, the visual analogue score VAS goes from 7.0-8.0 prior to the drug administration down to 1.0-2.0, and the duration of itching relief can last 2 to 8 h. As the time of drug use is extended, the itching relief duration is extended, and the use interval is extended, which does not show any drug dependence.

After 3 days of continuous application of the MAP gel medical device, 8 patients have their eczema areas fully healed, as indicated by disappearance of erythema, papules and blisters, and no exudation at the affected part. After 5 days of continuous spraying, all patients are cured (see Table 2).

TABLE 2

| | |
|---|---|
| Average onset time (min) | 3.8 ± 2.1 |
| Average VAS prior to use | 7.7 ± 0.5 |
| Average VAS after use | 1.3 ± 0.2 |
| Average itching relief duration (h) | 6.9 ± 2.1 |
| Average healing time (d) | 3.2 ± 1.0 |

Example 3: Use of MAP Gel Cosmetic in Treatment of Polymorphous Sunlight Eruption Take an MAP solution with concentration at 0.5 mg/ml, mix with polyethylene glycol and glycerin at a volumetric ratio of 2:1:2, then add water for injection in an equal volume to prepare an MAP gel cosmetic, wherein the MAP content is 0.1 mg/g.

Gather 10 patients with acute inflammatory reaction after sunbath, it is required that the affected parts of the selected patients include the face or limbs, and the affected areas are no smaller than 1% TBSA (total body surface area). The patients are diagnosed by dermatologists for test. The affected parts of the selected patients have erythema, edema or blisters. Apply the above MAP gel cosmetic at the affected part for 3 times per day, and evenly apply the gel on the surface of the affected part each time. After applied with the MAP gel cosmetic, mitigation of itching and pain occurs to all the 10 patients, the onset time varies from 3 to 20 min, and the itching or pain relief duration is 3-8 h after use. After applying the MAP gel cosmetic for 5 days, all the 10 patients of sunlight eruption have their affected parts healed. Erythema, edema or blisters disappear (see Table 3).

TABLE 3

| | |
|---|---|
| Average onset time (min) | 12.6 ± 3.7 |
| Average VAS prior to use | 4.9 ± 0.8 |
| Average VAS after use | 1.1 ± 0.4 |
| Average itching relief duration (h) | 5.6 ± 1.7 |
| Average healing time (d) | 4.0 ± 0.6 |

Example 4: Use of MAP Lotion Medical Device in Treatment of Polymorphous Sunlight Eruption Take an MAP solution with concentration at 2.0 mg/ml, mix with propanediol and glycerin at a volumetric ratio of 1:1:2, then add water for injection in an equal volume to prepare an MAP lotion medical device, wherein the MAP content is 0.25 mg/g.

Gather 10 patients with acute inflammatory reaction after sunbath, it is required that the affected parts of the selected patients include the face or limbs, and the affected areas are no smaller than 1% TBSA (total body surface area). The patients are diagnosed by dermatologists for test. The affected parts of the selected patients have erythema, edema or blisters. Apply the above MAP lotion medical device at the affected part for 3 times per day, and evenly apply the household chemical lotion on the surface of the affected part each time. After applied with the MAP lotion medical device, mitigation of itching and pain occurs to all the 10 patients, the onset time varies from 2 to 18 min, and the itching or pain relief duration is 3-10 h after use. After applying the MAP hydrogel cosmetic for 4 days, all the 10 patients of sunlight eruption have their affected parts healed. Erythema, edema or blisters disappear (see Table 4).

TABLE 4

| | |
|---|---|
| Average onset time (min) | 10.2 ± 2.6 |
| Average VAS prior to use | 5.2 ± 1.6 |
| Average VAS after use | 1.0 ± 0.7 |
| Average itching relief duration (h) | 6.6 ± 1.3 |
| Average healing time (d) | 3.5 ± 0.7 |

Example 5: Use of MAP Hydrogel Medical Device in Treatment of Deep Second Degree Burn Take an MAP solution, mix with Guar gum, propanediol and propanetriol at a volumetric ratio of 4:1:1:1, add water for injection, use citric acid to adjust to pH 5.0, and prepare an MAP hydrogel medical device with the MAP content at 1.5 mg/ml.

Gather 30 patients of deep second degree burn, it is required that more than two doctors jointly confirm that the patients have deep second degree burn, and the patients sign the informed consent form and then join the study. The total burn area is less than 30% TBSA (total body surface area), and the tested part has an area greater than 2% TBSA. Use the above MAP gel medical device (test group) and a commercial chitosan gel (control group) as a control to treat, randomly, the subjects. Both products are used once every other day in an amount that can evenly cover the affected part. All the wounds need to be thoroughly cleaned with a disinfectant prior to the use of the product for the test group and the control product.

Observe the redness and swelling (wound edge width) of wound edges of the wounds in the test group and the control group at the same day (Day 0) of joining the study, Days 4, 6, 10, and 14, respectively, and perform analysis using the chi-square test. In the case where the test level α is 0.05, the differences on Days 10 and 14 are statistically significant (see Table 5). It is believed that the MAP hydrogel medical device according to the present invention is better than the control product in mitigating redness and swelling. At the same time, it is further observed that the MAP hydrogel medical device according to the present invention has the effect of inhibiting exudation in the acute inflammation phase of burns and lowering the probability of growth of microorganisms.

TABLE 5

| Index | Test group | Control group | P value |
|---|---|---|---|
| Day 0 | | | 0.7640 |
| None | 4 (26.67%) | 5 (33.33%) | |
| Light | 4 (26.67%) | 2 (13.34%) | |
| Mild | 3 (20.00%) | 4 (26.67%) | |
| Severe | 4 (26.67%) | 4 (26.67%) | |
| Day 4 | | | 0.6895 |
| None | 5 (33.33%) | 6 (40.00%) | |
| Light | 5 (33.33%) | 4 (26.67%) | |
| Mild | 4 (26.67%) | 1 (6.67%) | |
| Severe | 1 (6.67%) | 4 (26.67%) | |
| Day 6 | | | 1.0083 |
| None | 5 (33.33%) | 7 (46.70%) | |
| Light | 6 (40.00%) | 3 (20.00%) | |
| Mild | 3 (20.00%) | 2 (13.33%) | |
| Severe | 1 (6.67%) | 3 (20.00%) | |
| Day 10 | | | 0.0429 |
| None | 12 (80.00%) | 8 (53.33%) | |
| Light | 2 (13.34%) | 2 (13.34%) | |
| Mild | 1 (6.67%) | 5 (33.33%) | |
| Severe | 0 (0.00%) | 0 (0.00%) | |
| Day 14 | | | 0.0376 |
| None | 13 (86.67%) | 7 (46.70%) | |
| Light | 2 (13.34%) | 3 (20.00%) | |
| Mild | 0 (0.00%) | 5 (33.33%) | |
| Severe | 0 (0.00%) | 0 (0.00%) | |

Example 6: Use of MAP Liquid Drug in Treatment of Deep Second Degree Burn

Take an MAP solution with concentration at 5 mg/ml, add 0.001% acetic acid in an equal volume to dilute to 2.5 mg/ml, the pH of the solution is 5.0, and form an MAP liquid drug with an MAP content of 2.5 mg/ml.

Gather 30 patients of deep second degree burn, it is required that more than two doctors jointly confirm that the patients have deep second degree burn, and the patients sign the informed consent form and then join the study. The total burn area is less than 30% TBSA (total body surface area), and the tested part has an area greater than 2% TBSA. Use the above MAP liquid drug (test group) and a commercial chitosan liquid product (control group) as a control to treat, randomly, the subjects. Both products are used once every other day in an amount that can evenly cover the affected part. All the wounds need to be thoroughly cleaned with a disinfectant prior to the use of the product for the test group and the control product.

Observe the redness and swelling (wound edge width) of wound edges of the wounds in the test group and the control group at the same day (Day 0) of joining the study, Days 4, 6, 10, and 14, respectively, and perform analysis using the chi-square test. In the case where the test level α is 0.05, the difference on Day 10 is statistically significant (see Table 6). It is believed that the MAP liquid drug according to the present invention is better than the control product in mitigating redness and swelling. At the same time, it is further observed that the MAP liquid drug has the effect of inhibiting exudation in the acute inflammation phase of burns and lowering the probability of growth of microorganisms.

TABLE 6

| Index | Test group | Control group | P value |
|---|---|---|---|
| Day 0 | | | 0.9592 |
| None | 4 (26.67%) | 5 (33.33%) | |
| Light | 4 (26.67%) | 2 (13.34%) | |
| Mild | 3 (20.00%) | 4 (26.67%) | |
| Severe | 4 (26.67%) | 4 (26.67%) | |
| Day 4 | | | 1.0743 |
| None | 6 (40.00%) | 6 (40.00%) | |
| Light | 5 (33.33%) | 3 (20.00%) | |
| Mild | 3 (20.00%) | 2 (13.34%) | |
| Severe | 1 (6.67%) | 4 (26.67%) | |
| Day 6 | | | 0.8739 |
| None | 7 (46.70%) | 7 (46.70%) | |
| Light | 5 (33.33%) | 3 (20.00%) | |
| Mild | 3 (20.00%) | 2 (13.33%) | |
| Severe | 0 (0.00%) | 3 (20.00%) | |
| Day 10 | | | 0.0420 |
| None | 11 (73.33%) | 8 (53.33%) | |
| Light | 3 (20.00%) | 2 (13.34%) | |
| Mild | 1 (6.67%) | 5 (33.33%) | |
| Severe | 0 (0.00%) | 0 (0.00%) | |

Example 7: Use of MAP Liquid Medical Device in Treatment of Shingles

Take an MAP solution, dilute with physiological saline, use acetic acid to adjust to pH 4.0, and obtain an MAP liquid medical device, wherein the MAP concentration is 5 mg/ml.

Figure 1:
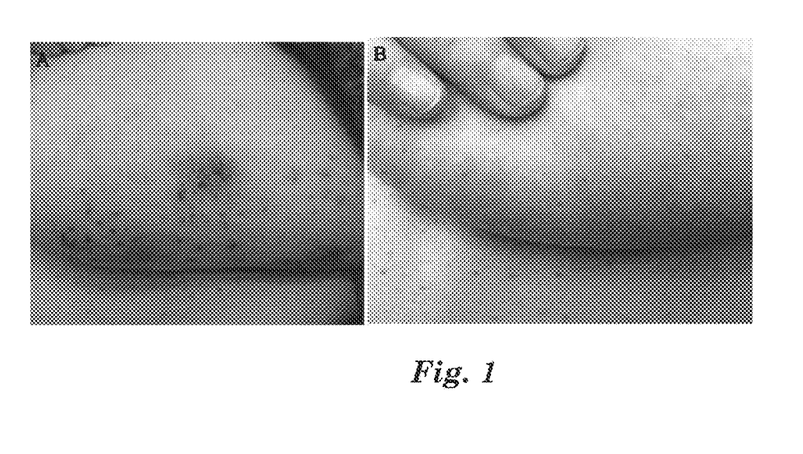
FIG. 1 illustrates results of herpes zoster treatment with the MAP liquid medical device according to the present invention and the control, wherein A, patients before the treatment; B, patients at 2 weeks after the treatment.

Select 15 patients of shingles, it is required that the affected areas are greater than 1% TBSA, the patients have a pain score≥4, and they are diagnosed by dermatologists before joining the study. Spray the MAP liquid medical device above at the affected part for 4 times per day. After sprayed with the MAP liquid medical device, the feeling of pain is weakened at the affected part within 1 min, and the duration of pain relief can last for 1.8 to 3 h on the 1st day of the use of the device. After 5 days of continuous spraying, the duration of pain relief is extended to 15 h, and the use interval is extended. After 7 days of continuous spraying of the MAP liquid medical device above, erythema and blisters of shingles on 9 patients disappear, and their skin lesions heal. After 14 days, erythema and blisters disappear for the other 6 patients, and their skin lesions heal (see FIG. 1).

Example 8: Use of MAP Hydrogel Disinfecting Product in Treatment of Shingles

Take an MAP solution, mix with Guar gum and propanetriol at a mass ratio of 2:1:1, dilute with physiological saline, use acetic acid to adjust to pH 4.0, and obtain an MAP hydrogel disinfecting product, wherein the MAP concentration is 5.0 mg/ml.

Select 15 patients of shingles, it is required that the affected areas are greater than 1% TBSA, the patients have a pain score≥4, and they are diagnosed by dermatologists before joining the study. Apply the above MAP hydrogel disinfecting product on the affected part for 4 times per day and at a dose that can evenly cover the affected part. After sprayed with the MAP hydrogel disinfecting product, the pain at the affected part subsides within 1 to 8 min (onset time), and the duration of pain relief can last 2.2 to 5.0 h. After 5 days of continuous use, the duration of pain relief is extended to 12-15 h, and the use interval is extended. After 7 days of continuous application of the MAP hydrogel disinfecting product, erythema and blisters of shingles on 10 patients disappear, and their skin lesions heal. After 10 days, erythema and blisters disappear for the other 5 patients, and their skin lesions heal (see Table 7).

TABLE 7

| | |
|---|---|
| Average onset time min | 6.2 ± 1.8 |
| Average VAS prior to use | 5.9 ± 1.3 |
| Average VAS after use | 1.0 ± 0.6 |
| Average itching relief duration (h) | 13.6 ± 1.3 |
| Average healing time (d) | 7.9 ± 1.4 |

Example 9: Use of MAP Liquid Cosmetic in Scar Pain Relief Treatment

Mix an MAP solution with sodium alginate and glycerin at a ratio of 3:2:1 to prepare a formulation, use citric acid to adjust to pH 4.2, and obtain an MAP liquid drug, wherein the MAP concentration is 10 mg/ml.

Select 16 patients with post-operative scar pain, there is no limitation to the position of the scars, but the scar pain score must be ≥4 (the VAS scoring method is used to score the patients' pain). The patients can join the groups for test only after being diagnosed by plastic & reconstructive surgeons. Apply the MAP liquid cosmetic above at the affected part for 1 time per day. After applied with the MAP liquid cosmetic, the pain subsides at the affected part within 3 min, and the duration of pain relief can last for 9 to 15 h on the 1st day of the drug use. After 5 days of continuous application, the duration of pain relief is extended to 48-96 h, and at the same time, inflammatory symptoms of the scars, such as redness and swelling, subside.

Example 10: Use of MAP Liquid Healthcare Product in Scar Pain Relief Treatment

Take an MAP solution, mix with propanediol at a ratio of 2:1, use acetic acid to adjust to pH 4.0, and obtain an MAP liquid healthcare product, wherein the MAP concentration is 10 mg/ml.

Figure 2:
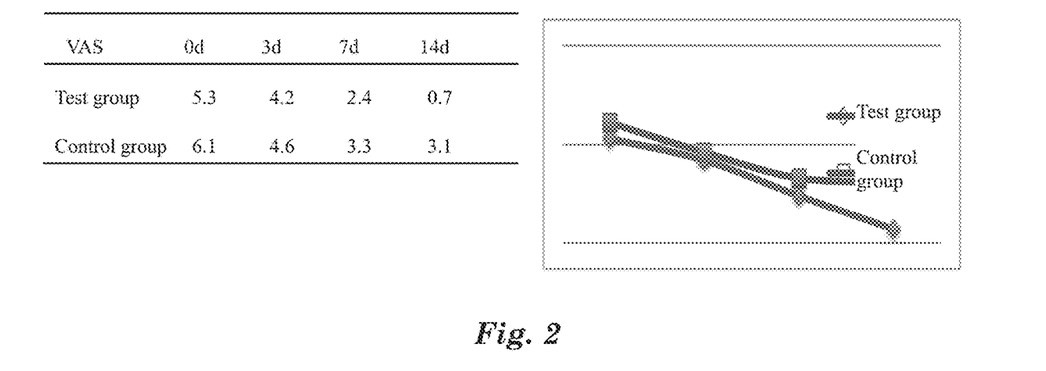
FIG. 2 illustrates the pain relief effect of the MAP liquid healthcare product according to the present invention in scar pain relief treatment.

Gather 10 patients with post-operative scar pain, there is no limitation to the position of the scars, but the scar pain score must be ≥4 (the VAS scoring method is used to score the patients' pain). The patients can join the groups for test only after being diagnosed by plastic & reconstructive surgeons. The patients are randomly divided into a control group and a test group, who apply physiological saline and the above MAP liquid healthcare product, respectively, at the affected part for 1 time per day. After spraying the MAP liquid healthcare product, record pain mitigation situations at Days 0, 3, 7 and 13, for the test group, the pain decreases from 5.3 when the group begins to 0.7 after the use, and the p value is 0.017 compared with the control group that decreases from 6.1 to 3.1, which is statistically significant ($\alpha=0.05$) (see FIG. 2). It proves that the MAP liquid healthcare product according to the present invention can mitigate the pain caused by shingles.

Example 11: Use of MAP Liquid Medical Device in Treatment of Operative Incisions Take an MAP solution, dilute with a borate aqueous solution to obtain an MAP liquid formulation, and the pH is 5.5, wherein the MAP concentration is 2.5 mg/ml.

Gather 20 patients, whose incisions are stitched up with surgical sutures after abdominal operations, for test. The patients are diagnosed by surgeons and then join the groups. They are randomly divided into two groups, the test group is treated with the above MAP liquid medical device, and the control group is treated with physiological saline. Spray to the affected part of the selected patients at 8 h after the surgery for 4 times per day. After sprayed with the MAP liquid medical device, 10 patients keep the body positions unchanged, and the pain is mitigated significantly within 20 min, the visual analogue VAS score goes from 7.0-9.0 prior to the use down to 2.0-3.0. After sprayed with physiological saline, the visual VAS scores of the 10 patients do not change, which does not show pain suppression.

The curing period of operative incisions of the 10 patients who use the MAP liquid medical device according to the present invention is 4 days, and there is no redness or swelling on the wound edge. The curing period of operative incisions of the 10 patients who use physiological saline is 6 days, and on Day 6, there is still slight redness and swelling on the wound edge (see Table 8).

TABLE 8

| | Test group | Control group |
|---|---|---|
| Average onset time (min) | 15.6 ± 3.7 | No mitigation |
| Average VAS prior to use | 8.2 ± 1.8 | 8.0 ± 1.5 |
| Average VAS after use | 2.4 ± 0.5 | 8.0 ± 0.6 |
| Average pain relief duration (h) | 8.6 ± 1.1 | None |
| Average healing time (d) | 3.9 ± 0.4 | 6.2 ± 0.7 |

Example 12: Use of MAP Hydrogel Disinfecting Product in Treatment of Operative Incisions Take an MAP solution, add carboxymethyl cellulose and glycerin at a volumetric ratio of 2:1:1, and obtain an MAP hydrogel disinfecting product, wherein the MAP concentration is 2.5 mg/ml.

Gather 20 patients, whose incisions are stitched up with surgical sutures after abdominal operations, for test. The patients are diagnosed by surgeons and then join the groups. They are randomly divided into two groups, the test group is treated with the above MAP hydrogel disinfecting product, and the control group is treated with a blank gel prepared by mixing carboxymethyl cellulose and glycerin. Spray to the affected part of the selected patients at 8 h after the surgery for 4 times per day. After applied with the MAP gel disinfecting product, 10 patients keep the body positions unchanged, and the pain is mitigated significantly within 18 min, the visual analogue VAS score goes from 7.0-9.0 prior to the use down to 2.0-3.0. After applied with the blank gel, the visual VAS scores of the 10 patients do not change, which does not show pain suppression.

The curing period of operative incisions of the 10 patients who use the MAP gel disinfecting product according to the present invention is 4 days, and there is no redness or swelling on the wound edge. The curing period of operative incisions of the 10 patients who use physiological saline is 6 days, and on Day 6, there is still slight redness and swelling on the wound edge (see Table 9).

TABLE 9

|  | Test group | Control group |
|---|---|---|
| Average onset time (min) | 14.0 ± 2.9 | No mitigation |
| Average VAS prior to use | 8.1 ± 1.6 | 8.0 ± 1.2 |
| Average VAS after use | 2.6 ± 0.8 | 7.8 ± 0.4 |
| Average pain relief duration (h) | 8.9 ± 1.6 | None |
| Average healing time (d) | 3.5 ± 0.4 | 6.0 ± 0.8 |

Example 13: Use of MAP Liquid Medical Device in Treatment of Chronic Skin Ulcer Take an MAP freeze-dried powder, use physiological saline to prepare a 1.0 mg/ml aqueous solution, use acetic acid to adjust pH to 4.8, and obtain an MAP liquid medical device.

Figure 3:
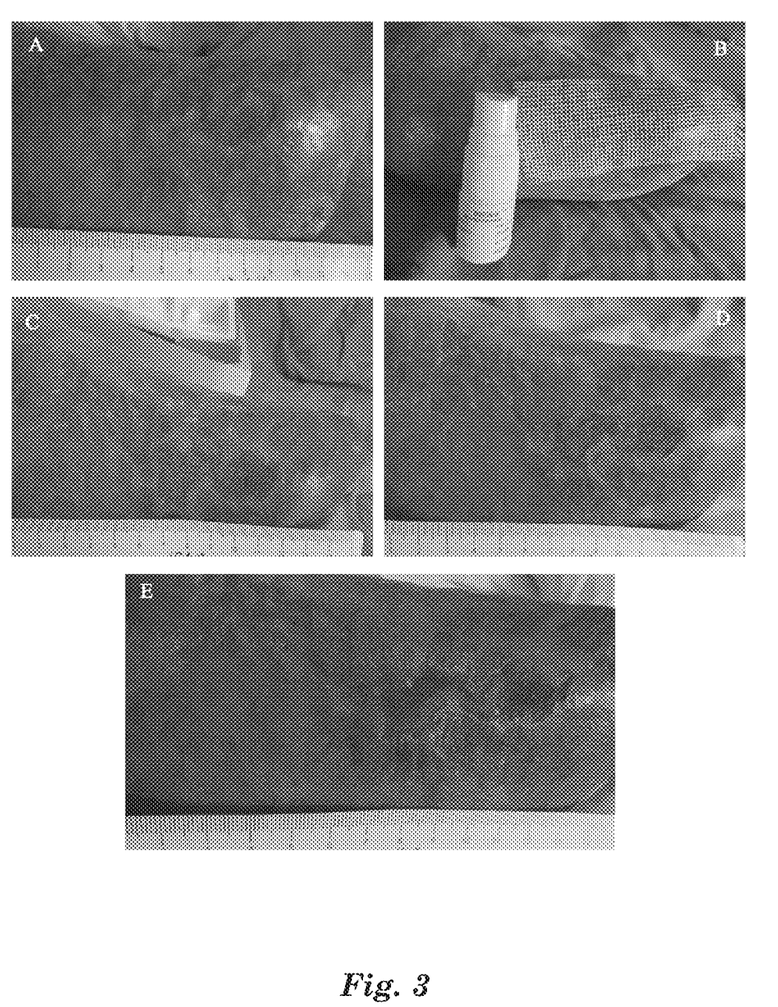
FIG. 3 illustrates the effect of the MAP liquid medical device according to the present invention in promoting wound surface healing in treatment of chronic skin ulcers, wherein A, patients at Day 0 of the treatment; B, the treatment method for the patients; C, patients at Day 7 of the treatment; D, patients at Day 10 of the treatment; E, patients at Day 15 of the treatment.

Gather 10 patients with chronic skin ulcers caused by skin inflammation or scars, the ulcer areas are between 15 and 20 square centimeters, with manifestations of red and swollen wound edges and failure of the wound surface to heal for more than 3 months. The patients join the groups for test after being diagnosed by plastic & reconstructive surgeons. Spray the MAP liquid medical device above for the selected patients for 2 times per day. After 10 days of use, 8 patients have the redness and swelling of the wound edge mitigated. After 16 days of use, 3 patients have the wound surface healed. After 21 days of use, the remaining 10 patients have the wound surface healed (see FIG. 3).

Example 14: Use of MAP Lotion Disinfecting Product in Treatment of Chronic Skin Ulcers Take an MAP solution, mix with propanetriol at a ratio of 1:1, use acetic acid to adjust to pH 4.8, and obtain an MAP lotion disinfecting product.

Gather 10 patients with chronic skin ulcers caused by skin inflammation or scars, the ulcer areas are between 15 and 20 cm$^2$, with manifestations of red and swollen wound edges and failure of the wound surface to heal for more than 3 months. The patients join the groups for test after being diagnosed by plastic & reconstructive surgeons. Spray the MAP lotion disinfecting product above for the selected patients for 2 times per day. All 10 patients have the chronic skin ulcers healed with an average healing time of 20.2±3.7 days. The wound base is covered by new epithelial tissues with no exudation at the surface.

Example 15: Use of MAP Mask Cosmetic in Treatment of Coarse Pores

Mix an MAP solution with Carrageenan and agar at a ratio of 2:2:1 to obtain an MAP mask stock solution, wherein the MAP concentration is 2.0 mg/ml. Take 20 ml of the MAP mask stock solution, and form an MAP mask cosmetic on silk paper.

Gather 15 patients who have coarse pores due to the use of color makeup, environmental pollution and other reasons, and who are diagnosed by dermatologists to have coarse pores. They have the manifestation of coarse pores and characterizations of inflammation, such as slight redness and swelling in the surrounding area.

Use the above MAP mask cosmetic once every other day, apply continuously for 25 min and then take it away, for a total of 10 times of use. On Day 7 of the application, the slight redness and swelling surrounding the pores are mitigated for all patients, and on Day 20, the pores shrink to normal, and there is no characterization of inflammation.

Example 16: Use of MAP Mask Medical Device in Treatment of Coarse Pores

Take a 1.0 mg/ml MAP solution as a mask stock solution, take 20 ml of the MAP mask stock solution, and form an MAP mask medical device on silk paper.

Gather 10 patients who have coarse pores due to the use of color makeup, environmental pollution and other reasons, and who are diagnosed by dermatologists to have coarse pores. They have the manifestation of coarse pores and characterizations of inflammation, such as slight redness and swelling in the surrounding area.

Use the above MAP mask medical device once per day, apply continuously for 25 min and then take it away, for a total of 10 times of use. On Day 6 of the application, the slight redness and swelling surrounding the pores are mitigated for all patients, and on Day 18, the pores shrink to normal, and there is no characterization of inflammation.

Example 17: Use of MAP Patch Medical Device in Treatment of Drug Rash (Dermatitis Medicamentosa)

Take an MAP solution, mix with polyvinyl alcohol, Guar gum, polyethylene glycol, and glycerin at a ratio of 2:1:1:0.2:0.2, use acetic acid to adjust to pH 6.5, and prepare an MAP patch stock solution, wherein the MAP concentration is 3.5 mg/ml. Take 25 ml of the MAP patch stock solution to combine with a non-woven fabric to form an MAP patch medical device.

Gather 24 patients of drug rash, the affected area is greater than 1% of the body surface area and the manifestation is red papules. All patients are diagnosed by dermatologists, fill up an informed consent form and then join the study. Use the above MAP patch medical device once per day, apply continuously for 30 min and then take it away. On Day 1 of the application, the itchy degree of the affected parts of the 24 patients begins to subside, and the visual analogue VAS score goes from 6.0-9.0 down to 2.0-3.0.

After 7 days of use, 8 patients have red papules completely disappeared. After 21 days of use, the remaining 16 patients have red papules completely disappeared (see Table 10).

TABLE 10

| Average VAS prior to use | 8.1 ± 1.5 |
|---|---|
| Average VAS after use | 2.4 ± 0.6 |
| Average healing time (d) | 17.9 ± 2.4 |

Example 18: Use of MAP Liquid Cosmetic in Treatment of Drug Rash (Dermatitis Medicamentosa)

Take an MAP solution, use acetic acid to adjust to pH 6.0, and obtain an MAP liquid cosmetic, wherein the MAP concentration is 1.5 mg/ml.

Gather 10 patients of drug rash, the affected area is greater than 1% of the body surface area and the manifestation is red papules. All patients are diagnosed by dermatologists, fill up an informed consent form and then join the study. Apply the MAP liquid cosmetic above 1 time in the morning and 1 time in the evening every day. On Day 1 of the use, the itchy degree of the affected parts of the 10 patients begins to subside, and the visual analogue VAS score goes from 7.0-9.0 down to 2.0-3.0. After 8 days of use, 5 patients have red papules completely disappeared. After 17 days of use, the remaining 5 patients have red papules completely disappeared (see Table 11).

TABLE 11

| | |
|---|---|
| Average VAS prior to use | 8.6 ± 1.9 |
| Average VAS after use | 2.3 ± 0.8 |
| Average healing time (d) | 13.5 ± 2.7 |

Example 19: Use of MAP Liquid Medical Device in Treatment of Psoriasis

Take an MAP solution, use acetic acid to adjust to pH 5.0, and obtain an MAP liquid medical device, wherein the MAP concentration is 1.5 mg/ml.

Gather 10 patients of psoriasis, the affected area is greater than 2% of the body surface area, and the manifestation is erythema with clear boundaries and various shapes and sizes, which are surrounded by inflammatory flush. There is slight infiltration and thickening, and the surface is covered by multiple layers of silver-white scales. It is easy to scratch off the scales, and when the scales are cleaned off, there is a translucent thin film that is light red and bright. If the thin film is broken, slight bleeding can be observed. All patients are diagnosed by dermatologists, fill up an informed consent form and then join the study. Use the MAP liquid medical device above for 3 times per day. On Day 1 of the use, the itchy degree of the affected parts of the 10 patients begins to subside, and the visual analogue VAS score goes from 6.0-7.5 down to 2.0-3.0. After 10 days of use, 3 patients have erythema completely disappeared. After 20 days of use, the remaining 7 patients have erythema completely disappeared (see Table 12).

TABLE 12

| | |
|---|---|
| Average VAS prior to use | 7.0 ± 0.5 |
| Average VAS after use | 2.4 ± 0.7 |
| Average healing time (d) | 16.4 ± 3.1 |

Example 20: Use of MAP Gel Drug in Treatment of Psoriasis

Take an MAP solution, mix with Carbomer, Carrageenan and propanetriol at a mass ratio of 1:2:1:1, use acetic acid to adjust to pH 5.0, and obtain an MAP gel drug, wherein the MAP concentration is 1.0 mg/ml.

Gather 10 patients of psoriasis, the affected area is greater than 2% of the body surface area, and the manifestation is erythema with clear boundaries and various shapes and sizes, which are surrounded by inflammatory flush. There is slight infiltration and thickening, and the surface is covered by multiple layers of silver-white scales. It is easy to scratch off the scales, and when the scales are cleaned off, there is a translucent thin film that is light red and bright. If the thin film is broken, slight bleeding can be observed. All patients are diagnosed by dermatologists, fill up an informed consent form and then join the study. Apply the MAP gel drug above for 3 times per day. On Day 1 of the use, the itchy degree of the affected parts of the 10 patients begins to subside, and the visual analogue VAS score goes from 6.5-7.8 down to 2.0-3.0. After 13 days of use, 5 patients have erythema completely disappeared. After 20 days of use, the remaining 5 patients have erythema completely disappeared (see Table 13).

TABLE 13

| | |
|---|---|
| Average VAS prior to use | 7.1 ± 0.6 |
| Average VAS after use | 2.3 ± 0.9 |
| Average healing time (d) | 15.6 ± 2.7 |

Example 21: Use of MAP Liquid Medical Device in Treatment of Seborrheic Dermatitis Take an MAP solution, use acetic acid to adjust to pH 5.0, and obtain an MAP liquid medical device, wherein the MAP concentration is 1.5 mg/ml. Pour the product into a pressure comb that can store liquids, and use the pressure comb to apply the MAP liquid medical device onto the scalp.

Gather 10 patients of seborrheic dermatitis, there is no limitation to the area of affected parts. The early manifestation is inflammatory papules around follicles. Subsequently as the disease develops, they become dark red patches that have relatively clear boundaries and are slightly yellow, which are covered by greasy scales or crusts. The patients feel slightly itching. All patients are diagnosed by dermatologists and then join the study. Use the MAP liquid medical device above for 3 times per day.

On Day 1 of the use, the itchy degree of the affected parts of the 10 patients begins to subside, and the visual analogue VAS score goes from 6.0-7.5 down to 2.0-3.0. After 10 days of use, 3 patients have erythema completely disappeared. After 20 days of use, the remaining 7 patients have erythema completely disappeared (see Table 14).

TABLE 14

| | |
|---|---|
| Average VAS prior to use | 7.0 ± 0.5 |
| Average VAS after use | 2.4 ± 0.7 |
| Average healing time (d) | 16.4 ± 3.1 |

Example 22: Use of MAP Hydrogel Cosmetic in Treatment of Seborrheic Dermatitis

Take an MAP solution, add carboxymethyl cellulose and Xanthan gum at a mass ratio of 2:1:1, and obtain an MAP hydrogel cosmetic, wherein the MAP concentration is 1.5 mg/ml.

Gather 10 patients of seborrheic dermatitis, there is no limitation to the area of affected parts. The early manifestation is inflammatory papules around follicles. Subsequently as the disease develops, they become dark red patches that have relatively clear boundaries and are slightly yellow, which are covered by greasy scales or crusts. The patients feel slightly itching. All patients are diagnosed by dermatologists and then join the study. Use the MAP hydrogel cosmetic above for 3 times per day. On Day 5 of the use, the itching of all the affected parts of the 10 patients subside, the inflammatory papules become lighter in color, and the patch area has a shrinking tendency. After 9 days of use, all the 10 patients have seborrheic dermatitis healed, and erythema completely disappear.

Example 23: Use of MAP Liquid Medical Device in Hair Transplant

Take an MAP solution, use acetic acid to adjust to pH 5.0, and obtain an MAP liquid medical device, wherein the MAP concentration is 1.0 mg/ml.

Gather 10 patients of male-pattern hair loss as diagnosed by plastic & reconstructive surgeons for artificial hair transplantation. The observation area of hair transplant is 1% of the body surface area. Test group: Prior to transplantation, 5 patients use the MAP liquid medical device above, and artificial hair is transplanted after 30 min. After hair transplant, spray the MAP medical device for 2 times per day. Control group: Prior to transplantation, spray physiological saline on 5 patients as the control, and after hair transplant, spray physiological saline for 2 times per day.

For the patients in the test group that use the MAP liquid medical device according to the present invention, the percent of successful hair transplant area in the overall hair transplant area is 95.1%±2.2%; for the patients in the control group that use physiological saline, the percent of successful hair transplant area in the overall hair transplant area is 72.8%±1.7%. It shows that MAP increases the success rate of hair transplant.

Example 24: Use of MAP Liquid Medical Device in Skin Grafting

Take an MAP solution, use acetic acid to adjust to pH 5.5, and obtain an MAP liquid medical device, wherein the MAP concentration is 1.2 mg/ml.

Gather 10 patients of degree III burns as diagnosed by burn surgeons, and use the autologous skin grafting for treatment. The observation area of skin grafting is 1% of the body surface area. Test group: Prior to skin grafting, 5 patients use the MAP liquid medical device above, and autologous particulate skin is grafted after 3 min. After skin grafting, spray the MAP medical device again, and provide a protection by covering after 3 min. Control group: Prior to skin grafting, spray physiological saline on 5 patients as the control, and after skin grafting, spray physiological saline again. Provide a protection by covering after 3 min.

For the patients in the test group that use the MAP liquid medical device according to the present invention, the percent of successful skin grafting area in the overall skin grafting area is 89.3%±1.9%; for the patients in the control group that use physiological saline, the percent of successful skin grafting area in the overall skin grafting area is 62.4%±3.2%. It shows that MAP increases the success rate of skin grafting.

Example 25: Use of MAP Liquid Medical Device in Male-Pattern Hair Loss

Take an MAP solution, use acetic acid to adjust to pH 4.5, and obtain an MAP liquid medical device, wherein the MAP concentration is 1.0 mg/ml.

Gather 10 patients of male-pattern hair loss as diagnosed by dermatologists. The manifestations include excess sebum secretion on the scalp, partial follicular necrosis, medium hair loss, and a need to wash hair every day.

Select 3 $cm^2$ to count the number of follicles before using the product. Wash the hair, use the MAP liquid medical device above for the 1st time, 2 times per day, and for each time, evenly spray to the entire scalp, and use continuously for 90 days. Chief complaints of the 10 patients: after the 1st time use, the sebum secretion decreases, and it is no longer necessary to wash hair every day. The product has an effect on controlling the oil. After 90 days of continuous use, count the number of follicles in the selected area again, and the number of follicles is increased by 35%±2.3%.

It shows that the MAP product can, on one hand, inhibit the excess sebum secretion in male-pattern hair loss, and on the other hand, repair dying follicles and treat hair loss.

The invention claimed is:

1. A method for treating regular acne or acne rosacea, the method comprising: administering externally to the skin of an individual having regular acne or acne rosacea an effective amount of a composition comprising a mussel adhesive protein ("MAP"), wherein said skin administering treats the regular acne or acne rosacea.

2. The method according to claim 1, wherein the MAP comprises one or more of the sub-types selected from the group: *Mytilus edulis* foot protein (mefp) subtypes mefp-1, mefp-2, mefp-3, mefp-4, mefp-5, and mefp-6; collagens pre-COL-P, pre-COL-D, pre-COL-NG; and mussel feet matrix proteins PTMP and DTMP.

3. The method according to claim 1, wherein the MAP comprises one or more of the sub-types selected from the group mefp-1, mefp-2, mefp-3, mefp-4, mefp-5 and mefp-6.

4. The method according to claim 1, wherein the MAP comprises mefp-1.

5. The method according to claim 1, wherein the MAP is present in the composition at a concentration of 0.1 to 15.0 mg/ml.

6. The method according to claim 1, wherein the composition is a liquid formulation, a gel formulation, a lotion, a paste, or a foam formulation, or the composition is administered in the form of a therapy patch.

7. The method according to claim 1, wherein the composition has a pH in the range of 1.0 to 7.0.

8. The method according to claim 1, wherein the composition has a pH in the range of 3.0 to 6.5.

9. The method according to claim 1, wherein the composition is a medicine, a cosmetic preparation, a disinfecting product, or a healthcare product.

10. The method according to claim 1, wherein the composition is a foam formulation comprising MAP as the main active ingredient and a foaming agent matrix material, said foaming agent matrix material being one or any combination of hydroxypropylmethyl cellulose, gelatin, polyethylene glycol, sodium dodecyl sulfate, sodium fatty alcohol polyoxyethylene ether sulfonate, corn gluten powder, and acrylamide.

* * * * *